US011814616B2

(12) United States Patent
Lammers et al.

(10) Patent No.: US 11,814,616 B2
(45) Date of Patent: Nov. 14, 2023

(54) METHODS OF INCREASING BIOMASS PRODUCTIVITY IN ALGAE CULTURES

(71) Applicant: ARIZONA BOARD OF REGENTS ON BEHALF OF ARIZONA STATE UNIVERSITY, Scottsdale, AZ (US)

(72) Inventors: Peter Lammers, Tempe, AZ (US); Mark Seger, Gilbert, AZ (US); Wonkun Park, Chandler, AZ (US); Nicholas Csakan, Mesa, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 75 days.

(21) Appl. No.: 16/767,948

(22) PCT Filed: Dec. 14, 2018

(86) PCT No.: PCT/US2018/065822
§ 371 (c)(1),
(2) Date: May 28, 2020

(87) PCT Pub. No.: WO2019/118913
PCT Pub. Date: Jun. 20, 2019

(65) Prior Publication Data
US 2020/0299634 A1   Sep. 24, 2020

Related U.S. Application Data

(60) Provisional application No. 62/599,214, filed on Dec. 15, 2017.

(51) Int. Cl.
*C12N 1/12* (2006.01)
*A01G 33/00* (2006.01)
*C12M 1/00* (2006.01)

(52) U.S. Cl.
CPC ............ *C12N 1/12* (2013.01); *A01G 33/00* (2013.01); *C12M 21/02* (2013.01)

(58) Field of Classification Search
None
See application file for complete search history.

(56) References Cited

U.S. PATENT DOCUMENTS

| 5,151,347 A * | 9/1992 | Delente ................ C12M 29/24 435/813 |
| 2012/0028338 A1* | 2/2012 | Bhatnagar ............... C12P 7/649 435/257.3 |
| 2015/0017705 A1 | 1/2015 | Ho |

OTHER PUBLICATIONS

Wang, J. et al. 2014. Mixotrophic cultivation of microalgae for biodiesel production: status and prospects. Applied Biochemistry and Biotechnology 172: 3307-3329; specif. p. 3311.*

Henkanatte-Gedera, S.M. et al. 2016. Removal of dissolved organic carbon and nutrients from urban wastewaters by Galdieria sulphuria: laboratory to field scale demonstration. Algal Research, pp. 1-7; < http://dx.doi.org/10.1016/j.algal.2016.08.001> specif. pp. 1, 2, 3, 4, 5.*

Smith, R.T. et al. 2015. Synergistic carbon metabolism in a fast growing mixotrophic freshwater microalgal species *Micractinium inermum*. Biomass and Bioenergy 82: 73-86; specif. pp. 73, 74, 75, 76, 81.*

Bader, K. et al., "Photosynthetic and respiratory oxygen gas exchange measured by mass spectrometry in the filamentous cyanobacterium Oscillatoria chalybea in dependence on the nitrogen source in the growth medium", Biochimica et Biophysica Acta (BBA)—Bioenergetics, May 1989, vol. 974, No. 3, pp. 303-310 <DOI:10.1016/S0005-2728(89)80248-8>.

Barbier, G. et al., "Comparative Genomics of Two Closely Related Unicellular Thermo-Acidophilic Red Algae, *Galdieria sulphuraria* and *Cyanidioschyzon merolae*, Reveals the Molecular Basis of the Metabolic Flexibility of Galdieriasulphuraria and Significant Differences in Carbohydrate Metabolism of Both Algae", Plant Physiology, Feb. 2005, vol. 137, No. 2, pp. 460-474 <DOI:10.1104/pp.104.051169>.

Graverholt, O. et al., "Heterotrophic high-cell-density fed-batch and continuous-flow cultures of Galdieria sulphuraria and production of phycocyanin", Applied Microbiology and Biotechnology, Nov. 2007 (available online Sep. 2007), vol. 77, pp. 69-75 <DOI:10.1007/s00253-007-1150-2>.

Gross, W. et al., "Characterization of a non-thermophilic strain of the red algal genus *Galdieria* isolated from Soos (Czech Republic)", European Journal of Phycology, Oct. 2002, vol. 37, No. 3, pp. 477-482 <DOI:10.1017/S0967026202003773>.

Gross, W. et al., "Cryptoendolithic growth of the red alga *Galdieria sulphuraria* in volcanic areas", European Journal of Phycology, 1998, vol. 33, No. 1, pp. 25-31 <DOI:10.1080/09670269810001736503>.

Gross, W. et al., "Ecophysiological Studies on the Red Alga *Galdieria sulphuraria* Isolated from Southwest Iceland", Plant Biology, Nov. 1999, vol. 1, No. 6, pp. 694-700 <DOI:10.1111/j.1438-8677.1999.tb00282.x>.

Gross, W. et al., "Heterotrophic Growth of Two Strains of the Acido-Thermophilic Red Alga *Galdieria sulphuraria*", Plant and Cell Physiology, Jun. 1995, vol. 36, No. 4, pp. 633-638 <DOI:10.1093/oxfordjournals.pcp.a078803>.

Gross, W. et al., "Purification and Characterization of a Galactose-1-Phosphate: UDP-Glucose Uridyltransferase from the Red Alga *Galdieria sulphuraria*", European Journal of Biochemistry, Nov. 1995, vol. 234, No. 1, pp. 258-263 <DOI:10.1111/j.1432-1033.1995.258_c.x>.

Gross, W., "Ecophysiology of algae living in highly acidic environments", Hydrobiologia, Aug. 2000, vol. 433, pp. 31-37 <DOI:10.1023/A:1004054317446>.

Heilmann, I. et al., "Mannose metabolizing enzymes from the red alga *Galdieria sulphuraria*", Phytochemistry, Jul. 1997, vol. 45, No. 5, pp. 903-906 <DOI:10.1016/S0031-9422(97)00081-2>.

(Continued)

*Primary Examiner* — Michael Barker
*Assistant Examiner* — Sharon M. Papciak
(74) *Attorney, Agent, or Firm* — BOOTH UDALL FULLER, PLC

(57) ABSTRACT

The present disclosure relates to methods of culturing algae that overcomes catabolic repression of photosynthesis in mixotrophic growth.

6 Claims, 5 Drawing Sheets

(56) References Cited

OTHER PUBLICATIONS

Heilmann, I. et al., "Polyphosphoinositide metabolism of Galdieria sulphuraria", Plant Physiology, Aug. 1997, vol. 114, Suppl. 3, p. 268, section 1390.

Oesterhelt, C. et al., "Characterization of a sugar/polyol uptake system in the red alga *Galdieria sulphuraria*", European Journal of Phycology, Aug. 1999, vol. 34, No. 3, pp. 271-277 <DOI:10.1080/09670269910001736322>.

Oesterhelt, C. et al., "Different Sugar Kinases Are Involved in the Sugar Sensing of Galdieria sulphuraria", Plant Physiology, Jan. 2002, vol. 128, No. 1, pp. 291-299 <DOI:10.1104/pp.010553>.

Oesterhelt, C. et al., "Regulation of photosynthesis in the unicellular acidophilic red alga *Galdieria sulphuraria*", The Plant Journal, Aug. 2007 (available online Jun. 2007), vol. 51, No. 3, pp. 500-511 <DOI:10.1111/i.1365-313X.2007.03159.x>.

Patent Cooperation Treaty, International Searching Authority, International Search Report for PCT/US2018/065822, 3 pages, dated Feb. 27, 2019.

Patent Cooperation Treaty, International Searching Authority, Written Opinion for PCT/US2018/065822, 5 pages, dated Feb. 27, 2019.

Scherer, S. et al., "Respiration of blue-green algae in the light", Archives of Microbiology, Oct. 1982, vol. 132, No. 4, pp. 329-332 <DOI:10.1007/BF00413384>.

Schmidt, R. et al., "Heterotrophic high cell-density fed-batch cultures of the phycocyanin-producing red alga *Galdieria sulphuraria*", Biotechnology and Bioengineering, Apr. 2005 (available online Feb. 2005), vol. 90, No. 1, pp. 77-84 <DOI:10.1002/bit.20417>.

Schonknecht, G. et al., "Gene Transfer from Bacteria and Archaea Facilitated Evolution of an Extremophilic Eukaryote", Science, Mar. 2013, vol. 339, No. 6124, pp. 1207-1210 <DOI:10.1126/science.1231707>.

Sorensen, L. et al., "Purification of the photosynthetic pigment C-phycocyanin from heterotrophic Galdieria sulphuraria", Journal of the Science of Food and Agriculture, Sep. 2013 (available online Feb. 2013), vol. 93, No. 12, pp. 2933-2938 <DOI:10.1002/jsfa.6116>.

Stadnichuk, I. et al., "Inhibition by glucose of chlorophyll a and phycocyanobilin biosynthesis in the unicellular red alga *Galdieria partita* at the stage of coproporphyrinogen III formation", Plant Science, Aug. 1998, vol. 136, No. 1, pp. 11-23 <DOI:10.1016/S0168-9452(98)00088-0>.

Toplin, J. et al., "Biogeographic and Phylogenetic Diversity of Thermoacidophilic Cyanidiales in Yellowstone National Park, Japan, and New Zealand", Applied and Environmental Microbiology, May 2008 (available online Mar. 2008), vol. 74, No. 9, pp. 2822-2833 <DOI:10.1128/AEM.02741-07>.

\* cited by examiner

METHODS OF INCREASING BIOMASS PRODUCTIVITY IN ALGAE CULTURES

RELATED APPLICATIONS

This application is the U.S. National Stage of International Application No. PCT/US2018/065822, filed on Dec. 14, 2018, which claims the benefit of and priority to U.S. Provisional Patent Application No. 62/599,214, filed Dec. 15, 2017, the contents of each of which are incorporated herein by reference in their entireties.

STATEMENT REGARDING FEDERALLY SPONSORED RESEARCH

This invention was made with government support under DE-EE0007562 awarded by the Department of Energy. The government has certain rights in the invention.

TECHNICAL FIELD

The present disclosure relates to a method of increasing biomass productivity in algae cultures. In particular, the methods herein provide a means of overcoming catabolic repression of photosynthesis in algae during mixotrophic and photoheterotrophic growth.

BACKGROUND

Large-scale algae cultivation is useful for a variety of purposes, which makes algae cultures an important starting point for the development of renewable resources and sustainability projects. Algae cultures may be factories for the production of food ingredients (for example, omega-3 fatty acids or natural antioxidants, food colorants, and dyes, such as phycocyanin, astaxanthin), food, fertilizer, bioplastics, chemical feedstock (raw material), nutraceuticals and pharmaceuticals. Biomass from algae cultures may also be a source of fuel feedstock. Additionally, algae cultures can be used to treat wastewater and thus is a means of pollution control.

However, the actual usefulness of algae cultures as a renewable resource has been limited by challenges in algae production. Typically, algae are cultured in open ponds or photobioreactors. While culturing algae in open ponds may be less expensive than setting up a photobioreactor, it is more difficult to control the culture conditions of open ponds. Accordingly, open pond cultures do not produce the best substrate yield. Additionally, open pond cultures are not always a feasible option, for example, in desert environments or where one cannot establish when there is limited water (such as in a desert environment) or limited space. In these circumstances, photobioreactors are the better way to culture algae. Still, photobioreactors cannot reach the scale of culturing as an open pond. Thus, in spite of photobioreactors having greater production per gram of algae, the total amount of biomass produced in a photobioreactor is less than the amount produced in an open pound culture. Another disadvantage of algae cultures in photobioreactors is photoinhibition as a result of photosynthesis oxygen accumulation. Whereas oxygen produced from photosynthesis can leave, excessive oxygen, particularly in a photobioreactor, and must be actively removed, often by a $N_2$ purge cycle. The need to purge the culture in a photobioreactor limits the length of the tubes of the photobioreactor due to the need to insert an out-gas station. Such a design limitation further increases the cost of culturing the algae. Accordingly, to more fully take advantage of the usefulness of algae as a renewable resource, methods of algae culture need to be improved to increase the rate of algae production in spite of the known limitations.

SUMMARY

The disclosure is directed to methods of increasing biomass productivity in an algae culture through the use of mixotrophic metabolism (simultaneous photosynthesis and respiration) coupled with restrictions on $O_2$ and $CO_2$ supply that result in higher substrate yields (grams biomass per gram of organic carbon substrate) in an algae culture. The methods comprise introducing a feedstock comprising a mixotrophic substrate to an algae culture medium; and providing no supplemental $O_2$ to the algae culture provided with enough light to support photosynthesis. The methods may further comprise not providing supplemental $CO_2$ to the algae culture when the algae culture is provided with a mixotrophic substrate and exposed to light in the above range of light intensity that is optimized for the intended cell concentration and mixing rate.

In some aspects, the stoichiometric oxygen supply of the algae culture is less than the stoichiometric carbon concentration introduced into the algae culture by the mixotrophic substrate in the feedstock.

The invention is also directed to methods of large-scale cultivation of algae. The methods comprise cultivating algae in a cultivation apparatus; providing a light source for cultivation; and not providing supplemental $O_2$ to the cultivation apparatus. In some embodiments, the methods further comprise administering a feedstock comprising a mixotrophic substrate to the cultivation apparatus. The methods may also comprise not providing supplemental $CO_2$ to the cultivation apparatus. In some aspects, the methods require that the stoichiometric oxygen supply in the cultivation apparatus is less than the stoichiometric carbon concentration introduced into the cultivation apparatus by the mixotrophic substrate in the feedstock. In some embodiments, the cultivation apparatus is a photobioreactor, for example, a tubular photobioreactor, a helical photobioreactor, or a glass tubular photobioreactor. However, any reactor that affords control over the entry of gases could be adapted to the invention.

The methods of the disclosure are applicable to both open and closed culture systems. The methods of the disclosure may further comprise mechanically mixing the algae culture or the algae in the cultivation apparatus. In some implementations, the algae of the methods are mixotrophic. In some embodiments, the algae are also thermophilic, acidophilic, or both. For example, the algae are red algae, such as a member of the Cyanidiales order or a *Galdieria* species. In one embodiment, the algae are *Galdieria sulphuraria*. In some aspects, the feedstock comprising a mixotrophic substrate may be wastewater, for example, wastewaters derived from food processing, food waste diversion programs, wastewaters from the production of beer, wine, distillers, beverage and bottling companies, and other wastewater sources of organic carbon including dairies, feedlots, swine and poultry production. In some implementations, the feedstock provides an excess amount of mixotrophic substrate relative to the cultivation time period for the algae culture or algae in the cultivation apparatus.

DETAILED DESCRIPTION

Figure 1:
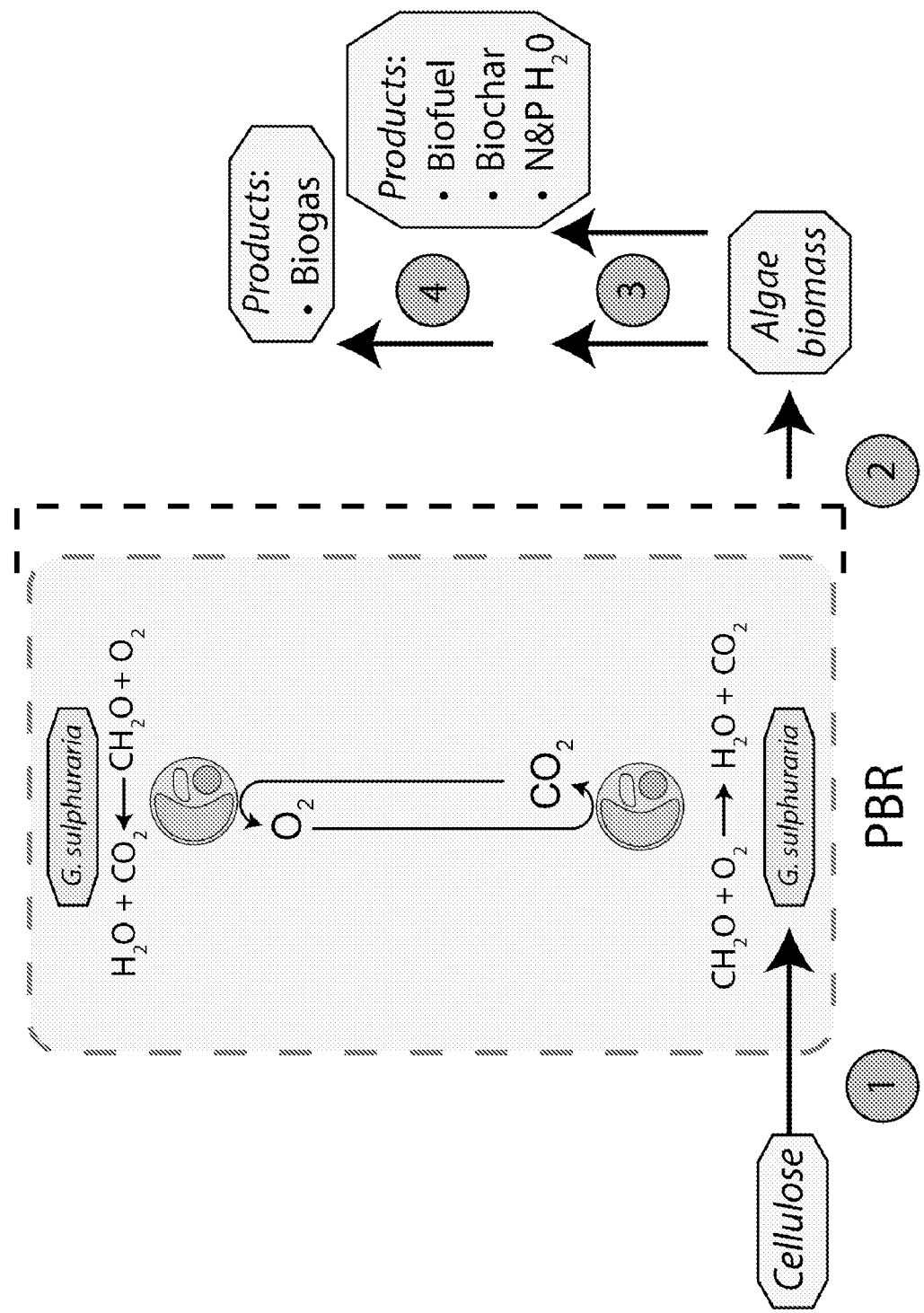
FIG. 1 depicts the schematic for the conversion of mixotrophic substrates into algae biomass, which can be the source of pigments, vitamins, lipids, proteins, carbohydrates, biochar for carbon sequestration or soil supplementation.

Detailed aspects and applications of the invention are described below in the drawings and detailed description of the invention. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the invention. It will be understood, however, by those skilled in the relevant arts, that the present invention may be practiced without these specific details. It should be noted that there are many different and alternative configurations, devices and technologies to which the disclosed inventions may be applied. The full scope of the inventions is not limited to the examples that are described below.

The singular forms "a," "an," and "the" include plural referents unless the context clearly dictates otherwise. Thus, for example, reference to "a step" includes reference to one or more of such steps.

As used herein, the term "algae" refers to microalgae, which are unicellular species of algae. Algae referenced in the disclosure includes both green and red algae and cyanobacteria. In some embodiments, the algae are red algae, for example in the order Cyanidiophyceae or the genus *Galdieria*. In some aspects, the algae are mixotrophs, extremophiles, or both. For example, the algae are mixotrophic and prefer high temperature and low pH in its growing environment.

As used herein, the term "light" refers to natural sunlight, natural sunlight with an artificial light source, or only an artificial light source. Preferably, light is provided at an intensity of above 50 µmol photosynthetically active radiation per square meter per second. As used herein, the description "enough light to support photosynthesis" or "an amount of light sufficient to support photosynthesis" refers to light at an intensity at least 50 µmol photosynthetically active radiation per square meter per second, for example, between 50 and 2,500 µmol photosynthetically active radiation per square meter per second. As it is well known in the art, the cell density and the mixing rate of an algae culture affects the minimum light intensity required to support photosynthesis. In some aspects, light is provided at an intensity of above 50, about 100, above 150, above 200, above 300, above 400, above 500, above 600, above 700, above 800, above 900, above 1000, above 1100, above 1200, above 1300, above 1500, above 1750, above 2000, above 2250, or above 2500 µmol photosynthetically active radiation per square meter per second. In another aspect, light is provided at an intensity of between 150 and that of full direct sunlight, which can be at or greater than 2500 µmol photosynthetically active radiation per square meter per second. For example, light is provided at an intensity of is between 50 and 2500, between 50 and 2000, between 50 and 1500, between 50 and 1300, between 50 and 1000, between 50 and 750, between 50 and 500, between 100 and 2500, between 100 and 2000, between 100 and 1500, between 100 and 1300, between 100 and 1000, between 100 and 750, between 100 and 500, between 150 and 2500, between 150 and 2000, between 150 and 1500, between 150 and 1300, between 150 and 1000, between 150 and 750, between 150 and 500, between 200 and 2500, between 150 and 2000, between 150 and 1500, between 200 and 1300, between 200 and 1000, between 200 and 750, between 200 and 500, between 300 and 2500, between 150 and 2000, between 150 and 1500, between 300 and 1300, between 300 and 1000, between 300 and 750, between 300 and 500, between 500 and 1500, between 500 and 1300, between 500 and 1000, between 750 and 1500, between 750 and 1300, or between 750 and 1000 µmol photosynthetically active radiation per square meter per second.

As herein, the term "mixotrophic metabolism" refers to an organism's simultaneous use of light and external reduced carbon sources to grow. In the context of algae, mixotrophic metabolism refers to the simultaneous dependence on photosynthesis and cellular respiration to grow and accumulate biomass.

As used herein, the term "mixotrophic substrate" refers to sugars, sugar alcohols, oligosaccharides, polysaccharides amino acids, and fatty acids. For example, D-glucose, D-mannose, D-galactose, D-fructose, L-sorbose, D-fucose, L-fucose, L-rhamnose, D-arabinose, L-arabinase, D-lyxose, D-ribose, D-xylose, L-xylose, D-manitol, D-sorbitol, dulcitol, L-fucitol, adonitol, xylitol, L-arabitol, D-arbitol, glycerol, sucrose, oligosaccharides and polysaccharides with the aforementioned monomers, all amino acids, and acetate. In some aspects, "mixotrophic substrate" encompasses cellulosic sugars.

As used herein, the term "photosynthetically active radiation" is abbreviated as PAR.

As used herein, the term "substrate yield" is expressed as grams of biomass per gram of carbon substrate. While the term is typically associated with fermentation, it is also used in relation to mixotrophic metabolism. For mixotrophic metabolism, the measurement of biomass produced is limited to the time interval in which a mixotrophic substrate is present in the culture.

As used herein, the term "supplemental oxygen" or "supplemental $O_2$" refers to any external source of oxygen and thus excludes oxygen produced by the organism from photosynthesis. In certain implementations, the requirement of not providing supplemental oxygen to an algae culture is satisfied by culturing the algae in a closed system.

As used herein, the term "supplemental carbon dioxide" or "supplemental $CO_2$" refers to any external source of $CO_2$. Accordingly, supplemental $CO_2$ does not to the $CO_2$ produced from cellular respiration. In certain implementations, the requirement of not providing supplemental $CO_2$ to an algae culture is satisfied by culturing the algae in a closed system.

This disclosure relates to the discovery of a previously unknown capacity of mixotrophic algae to sustain photosynthesis while metabolizing mixotrophic substrates via respiration without the addition or presence of external sources of metabolic gases ($O_2$ and $CO_2$). By taking advantage of mixotrophic algae's capacity for mixotrophic metabolism, the amount of biomass product produced is increased. Thus, this disclosure is directed to methods of increasing biomass productivity in an algae culture. These methods are applicable to culturing in both open and closed culture systems.

Figure 2:
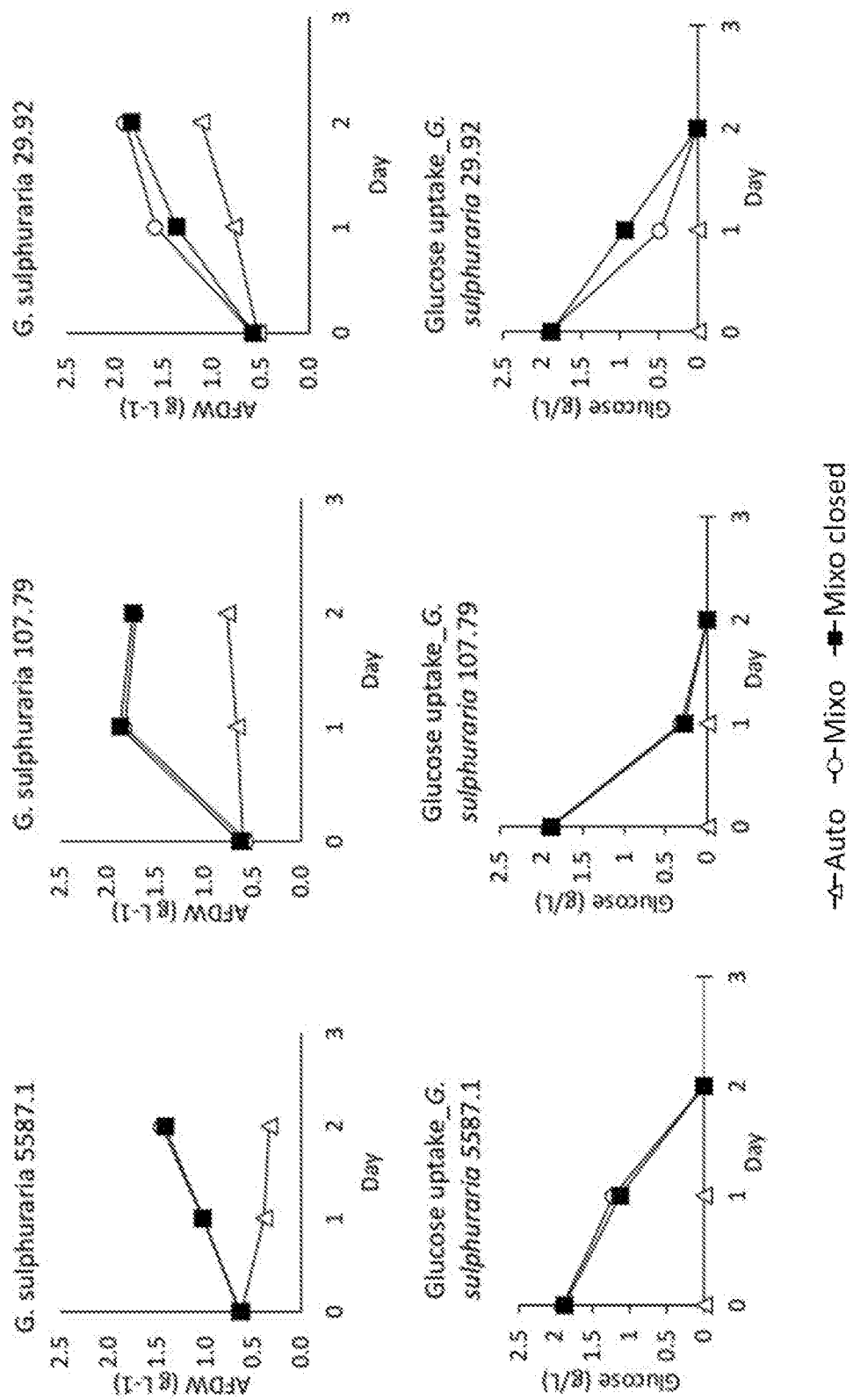
FIG. 2 depicts growth and glucose uptake of three *Galdieria* strains under autotrophic, aerobic, and microaerobic (closed) conditions. Top row: growth, as measured by ash-free dry weight (AFDW). Bottom row: glucose uptake. The results shown are the mean of triplicate cultures for each treatment, error bars show the standard deviation of the mean.

Mixotrophic algae species experience catabolic repression of photosynthesis, for example, due to excess accumulation of $O_2$ and other respiratory metabolites (Oesterhelt et al. and Stadnnichuk et al.). Accordingly, an algae culture suitable for biomass production via photosynthesis has its productivity limited to the limits of photosynthesis. However, it was discovered that catabolic repression of photosynthesis in algae can be circumvented by limiting the amount of metabolic gas, specifically $O_2$, in the culture. The novelty of the method lies in imposing a requirement on the cultivated algae to maintain photosynthetic oxygen evolution as the major source of oxidant for respiration of mixotrophic substrates (e.g. sugars, sugar alcohols, oligo- and poly-saccharides and amino acids). As shown in FIG. 1, the stoichiometry between $O_2$ and $CO_2$ synthesis and consumption is 1:1 when the respiration-dependent metabolic rate is coupled to the photosynthesis-dependent metabolic rate. This only happens when external supplies of $O_2$ are limited. This oxygen-limited, metabolic state favors mixotrophic algae cells over contaminating heterotrophic cells that might otherwise have faster growth rates because the mitochondria in algae cells will have immediate access to photosynthetic $O_2$ (Bader and Schmid). Accordingly, in some implementations, the method of increasing biomass productivity in an algae culture described herein does not comprise providing supplemental oxygen to the algae culture. In fact, in some aspects of the method described herein, no supplemental oxygen is provided to the algae culture, even where the algae culture is a closed system.

Where the algae culture is provided sufficient light to support photosynthesis, no supplemental $CO_2$ is required. Under conditions where the amount of light provided supports photosynthesis, the complete oxidation of a mixotrophic substrate to $CO_2$ provides the only source of $CO_2$ for photosynthetic $CO_2$ assimilation. As shown in FIG. 1, respiratory $CO_2$ released from sugar oxidation in cultures deprived of exogenous metabolic gases is re-captured via photosynthesis. This was demonstrated in sealed-tube cultures in the presence and absence of DCMU (3-(3,4-dichlorophenyl)-1,1-dimethylurea), an inhibitor of photosystem II (FIG. 2). The abundant growth observed in sealed cultures (no external $O_2$) was eliminated when DCMU is present. Tabular results for autotrophic and heterotrophic controls are shown in Table 1. Data are provided for mixotrophic cultures plus autotrophic and heterotrophic controls incubated with (+) and without (−) the addition of the photosystem II inhibitor DCMU. Heterotrophic substrate yields (grams of biomass per gram of mixotrophic substrate) in open cultures were in the expected range reported in the literature 0.4 to 0.49 range (Graverholt and Eriksen, Sorensen et al.). Two different *G. sulphuraria* strains manifested substrate yields of 0.71 and 1.02 g-biomass/g-sugar. In the case of sealed-tube mixotrophic cultures with DCMU the high apparent substrate yields without any biomass growth are interpreted as glucose uptake without any subsequent glucose metabolism, since glucose uptake was unaffected by the DCMU (data not shown). Thus, in some implementations, the method described herein does not comprise providing supplemental $CO_2$ to the algae culture. For example, to ensure the growth conditions favor mixotrophic metabolism, no supplemental oxygen, supplemental $CO_2$, or both is provided to the algae. As such, another novel advantage of the method described herein is that the method eliminates the engineering requirements for external $O_2$ and $CO_2$ supply, which simplifies the design of photobioreactors.

TABLE 1

Productivity and substrate yields for open and closed cultures for two strains of *Galdieria sulphuraria*

| Strain | Treatment | | Δbiomass (g/L) | Δglucose (g/L) | Sub. Yield (g biomass/g glucose) | Average Growth rate (g/L/day) |
|---|---|---|---|---|---|---|
| 074G | Open | Auto− | 3.55 | N/A | N/A | 0.51 |
| | | Auto+ | 0.08 | N/A | N/A | 0.01 |
| | | Mixo− | 5.03 | −7.49 | 0.67 | 0.72 |
| | | Mixo+ | 2.50 | −7.49 | 0.33 | 0.36 |
| | | Hetero− | 2.85 | −7.49 | 0.38 | 0.41 |
| | | Hetero+ | 2.82 | −7.49 | 0.38 | 0.41 |
| | Closed | Auto− | 0.48 | N/A | N/A | 0.07 |
| | | Auto+ | 0.13 | N/A | N/A | 0.02 |
| | | Mixo− | 5.33 | −7.49 | 0.71 | 0.77 |
| | | Mixo+ | 0.70 | −0.94 | 0.75 | 0.10 |
| | | Hetero− | 0.26 | −0.62 | 0.43 | 0.04 |
| | | Hetero+ | 0.22 | −0.56 | 0.39 | 0.03 |
| 87.1 | Open | Auto− | 4.22 | N/A | N/A | 0.62 |
| | | Auto+ | 0.06 | N/A | N/A | 0.01 |
| | | Mixo− | 6.75 | −7.11 | 0.95 | 1.00 |
| | | Mixo+ | 3.80 | −8.079 | 0.47 | 0.56 |

TABLE 1-continued

Productivity and substrate yields for open and closed cultures for two strains of Galdieria sulphuraria

| Strain | Treatment | | Δbiomass (g/L) | Δglucose (g/L) | Sub. Yield (g biomass/g glucose) | Average Growth rate (g/L/day) |
|---|---|---|---|---|---|---|
| | | Hetero− | 4.00 | −8.08 | 0.49 | 0.59 |
| | | Hetero+ | 3.99 | −8.079 | 0.49 | 0.59 |
| | Closed | Auto− | 0.79 | N/A | N/A | 0.12 |
| | | Auto+ | −0.21 | N/A | N/A | −0.03 |
| | | Mixo− | 8.20 | −8.05 | 1.02 | 1.21 |
| | | Mixo+ | 0.95 | −2.36 | 0.40 | 0.14 |
| | | Hetero− | 0.20 | −1.85 | 0.11 | 0.03 |
| | | Hetero+ | 0.18 | −2.01 | 0.09 | 0.03 |

Thus, in one embodiment, the method comprises providing an algae culture comprising mixotrophic algae species; and not providing supplemental $O_2$ to the algae culture when the algae culture. In some aspects, the oxygen supply to the algae culture is less than the stoichiometric requirement for oxidation of the mixotrophic substrate. However, one exception to this condition would be an optional short-duration supply of $O_2$ at night in the absence of a supplemental light source in the presence of a mixotrophic substrate. The exception could be avoided by limiting the quantity of mixotrophic substrate added such that it will be completely consumed during the light period. Accordingly, during lighted periods the stoichiometric ratio of oxygen introduced into the culture and the carbon supplied from the mixotrophic substrate is less than one.

The control of oxygen concentration in the algae culture may be mediated by providing no supplemental $O_2$ to the culture at all or only when culture is exposed to light, in particular sufficient light to support photosynthesis. Although specific the intensity of light that is sufficient to support photosynthesis is dependent on the cell density of the algae culture and the mixing rate of the culture, in some aspects, the intensity of light sufficient to support photosynthesis is above, 50, above 100, above 150, above 200, above 300, above 400, above 500, above 600, above 700, above 800, above 900, above 1000, above 1100, above 1200, above 1300, above 1500, above 1750, above 2000, above 2250, or above 2500 µmol photosynthetically active radiation per square meter per second. For example, the intensity of light is between 150 and 2500, between 150 and 2000, between 150 and 1500, between 150 and 1300, between 150 and 1000, between 150 and 750, between 150 and 500, between 200 and 2500, between 150 and 2000, between 150 and 1500, between 200 and 1300, between 200 and 1000, between 200 and 750, between 200 and 500, between 300 and 2500, between 150 and 2000, between 150 and 1500, between 300 and 1300, between 300 and 1000, between 300 and 750, between 300 and 500, between 500 and 1500, between 500 and 1300, between 500 and 1000, between 750 and 1500, between 750 and 1300, or between 750 and 1000 µmol photosynthetically active radiation per square meter per second. Thus, in some implementations, if the intensity of light is not above 150, above 200, above 300, above 400, above 500, above 600, above 700, above 800, above 900, above 1000, above 1100, above 1200, above 1300, above 1500, above 1750, above 2000, above 2250, or above 2500 µmol photosynthetically active radiation per square meter per second or not between 150 and 2500, between 150 and 2000, between 150 and 1500, between 150 and 1300, between 150 and 1000, between 150 and 750, between 150 and 500, between 200 and 2500, between 150 and 2000, between 150 and 1500, between 200 and 1300, between 200 and 1000, between 200 and 750, between 200 and 500, between 300 and 2500, between 150 and 2000, between 150 and 1500, between 300 and 1300, between 300 and 1000, between 300 and 750, between 300 and 500, between 500 and 1500, between 500 and 1300, between 500 and 1000, between 750 and 1500, between 750 and 1300, or between 750 and 1000 µmol photosynthetically active radiation per square meter per second, supplemental $O_2$ is provided to the culture. When the culture is provided with a mixotrophic substrate(s) and is not exposed to light sufficient to support photosynthesis, the method further comprises not providing supplemental $CO_2$ to the culture.

While the goal is to limit the amount of metabolic gases in the culture, such as by providing no supplemental $O_2$, $CO_2$, or both to the culture, the algae culture has access to both $O_2$ and $CO_2$ from its metabolic processes and thus are sustainable on only deliberate introduction of mixotrophic substrates. Accordingly, the method described herein further comprises introducing a feedstock comprising a mixotrophic substrate to the algae culture. Photosynthetic oxygen evolution in the chloroplast becomes the primary source of $O_2$ required for respiratory metabolism in mitochondria. Oxidation of mixotrophic substrates in the mitochondria releases $CO_2$ for use in the chloroplast. In fact, when glucose was present in the culture medium, the provision of $CO_2$ could be stopped without having any effect on culture growth or substrate yields. Intracellular re-utilization of $CO_2$ was previously documented by Scherer and Boger. Accordingly, the algae culture does not need to be in completely anaerobic conditions.

While metabolic gases do not need to be deliberately introduced into the culture (which reduces that capital costs of establishing the culture system), the culture also does not need to be mixed to circulate the oxygen produced from algae undergoing photosynthesis to the rest of the algae culture. Thus, in some implementations, the culture is mechanically mixed, while in other implementations, the culture is not mixed. If the algae culture is mixed, the mixing step cannot involve gas dispersion. The algae culture may be in an open culture system or a closed culture system.

The advantages of the described method include (1) circumvention of catabolic repression of photosynthesis by respiratory metabolites (Oesterhelt et al. and Stadnnichuk et al.); (2) increased substrate yields (grams biomass/grams glucose); (3) elimination of costs and technical difficulties associated with metabolic gas delivery are eliminated; (4) reduced risk of heterotrophic contamination and growth advantage to non-heterotrophic algae in culture due to direct intracellular O$_2$ utilization; (5) reduced capital cost and total operating expenses as well as operating costs per gram of biomass produced; and (6) reduced greenhouse gas emissions from lower energy consumption.

The method described herein can be implemented at any scale. Thus, in another embodiment, the method is directed to large-scale cultivation of algae, for example in a cultivation apparatus. The method comprises cultivating algae in a cultivation apparatus; providing light to the cultivation apparatus; and not providing supplemental O$_2$ to the cultivation apparatus. In some aspects, the stoichiometric oxygen supply of the algae culture is less than the stoichiometric carbon concentration introduced into the algae culture by the mixotrophic substrate in the feedstock. Accordingly, the stoichiometric ratio of oxygen introduced into the culture and the carbon supplied from the mixotrophic substrate is less than one. The cultivation apparatus can also be an open culture system or a closed culture system. In some implementations, the method does not comprise providing supplemental CO$_2$ to the cultivation apparatus. In some aspects, the method further comprises administering a feedstock comprising a reduced carbon source to the cultivation apparatus. In some aspects, the cultivation apparatus is a photobioreactor, for example, a tubular photobioreactor, a helical tubular photobioreactor, or a glass tubular photobioreactor. The cultivation apparatus may be an open culture system or a closed culture system. While mechanically mixing the algae in the cultivation apparatus is not always required, in some embodiments, the methods further comprise mechanically mixing the algae in the cultivation apparatus.

In the methods of the present disclosure, mixotrophic substrates in the feedstock may be selected from the group consisting of sugars, sugar alcohols, oligosaccharides, polysaccharides, amino acids, and fatty acids (see Schonknecht et al.). In some aspects, the feedstock comprises cellulosic sugars, amino acids, or both. As the methods of invention circumvents catabolic repression of photosynthesis, the amount of sugars in the feedstock, for example the amount of glucose, may be in excess. Depending on the algae in the culture, the feedstock is or is not acidic. For feedstock that is not acidic but should be acidic for optimal algae growth, the pH of the feedstock may be lower by the addition of mineral acids. In other aspects, the feedstock comprising a mixotrophic substrate may be wastewater or waste from a waste stream, for example, wastewaters derived from food processing, food waste diversion programs, wastewaters from the production of beer, wine, distillers, beverage and bottling companies, and other wastewater sources of organic carbon including dairies, feedlots, swine and poultry production. Accordingly, the methods are also directed to methods of wastewater treatment.

The algae may be mixotrophic red algae or green algae. As a non-limiting example, in some implementations the red algae culture comprises members of the Cyanidiophyceae, such the genus of *Galdieria*. The Cyanidiophyceae, especially those in the *Galdieria* genus require acidic pH conditions (for example, 0.5 to 4.0) and prefer elevated temperatures (40-50° C.). These conditions discourage the growth of heterotrophic bacteria, yeast and fungi that overtake mixotrophic cultures grown at neutral pH and lower temperatures. Accordingly, acidic wastewater, such as that from yogurt or soft drink production are suitable feedstock for Cyanidiophyceae cultures. To reduce the risk of contamination, the algae culture preferably comprises thermophilic, acidophilic algae species, or both.

The increased biomass yield of algae cultivation according to the methods of the present disclosure are useful for a variety of industries. For example, there is wide interest in the heat-stable phycocyanin (a blue pigment) from *Galdieria* for use as a food supplement, as an organic ink component and as a high-value fluorescent tag. Mixotrophic production of *Galdieria* biomass enables large-scale natural manufacture of this blue pigment. The methods of the present disclosure also enable shorter hydraulic residence times for algae-based wastewater treatment. This may be accomplished by combining waste mixotrophic substrates with high-strength wastewater (high N and P; for example, anaerobic digester wastewater, and landfill leachate). Examples of waste mixotrophic substrate sources include diverted food waste projects, dairy wastewater, food processing wastewater, fermentation and distillery wastes, beverage waste, fish cultivation wastewater. After mixing the N & P wastes and the waste mixotrophic substrate sources provide all the necessities for our low-O2 mixotrophic cultivation patent. For the above wastewaters that are food-grade, the algae biomass could be used in formulation of food pellets (for example, fish meal replacement) as a source of protein, carbohydrate, lipids, antioxidants, or fatty acids.

Examples

The present disclosure is further illustrated by the following examples that should not be construed as limiting. The contents of all references, patents, and published patent applications cited throughout this application, as well as the Figures, are incorporated herein by reference in their entirety for all purposes.

1. Culture Conditions

Experiments were performed on strains of *Galdieria sulphuraria* (5587.1, 107.79, and 29.92). The cultures were incubated in a lighted incubator (Percival Scientific, IA, USA) supplemented with 2% CO$_2$ under continuous light (150 µmol photons/m$^2$/s).

Seed cultures were prepared in tissue culture flasks (50 mL) and incubated on a shaker placed at 40° C. in the lighted incubator. Small-scale test cultures for testing were incubated under three conditions: autotrophic, mixotrophic (oxygenated), and mixotrophic (microaerobic in sealed tubes). For mixotrophic closed conditions, cultures were placed in 15 mL centrifuge tubes with screw caps that allowed for no air exchange. A modified Cyanidium medium (CM) at pH 1.0 (Toplin et al.) containing more nitrogen and phosphorus was used for mixotrophic scale up and experiments to support the additional growth. The composition of the medium, per liter, was as follows: (NH$_4$)$_2$SO$_4$, 2.64 g; KH$_2$PO$_4$, 0.20 g; NaCl, 0.12 g; MgSO$_4$·7H$_2$O, 0.25 g; CaCl$_2$·2H$_2$O, 0.07 g; Nitch's Trace Element Solution, 0.5 mL; FeCl$_3$ (solution=0.29 g/L), 1.0 mL. Glucose (5 or 12 mM) was amended to the medium for mixotrophic conditions.

Before the experiment, cell densities of the seed cultures were measured spectrometrically and then cells were harvested by centrifugation followed by a washing step. Pellets were resuspended in their corresponding medium (i.e. with or without sugar) targeting an initial cell density of 0.5 g/L (using a 0.4 conversion factor from O.D.750 to g/L). Master mixes for each condition were aliquoted (6.0 mL) into culture tubes. Borosilicate tubes with closures that allowed for air exchange were used for cultures placed under both autotrophic and mixotrophic open conditions. Tubes were cultivated using a roller drum at 40° C. in the same lighted incubator described above and supplemented with 2% $CO_2$ under continuous light (150 µmol photons/m²/s).

Large scale cultures were tested in photobioreactors. For the flat-panel photobioreactor (flat panel PBR), the culture medium comprised corn stover hydrolysate, and the culture was supplemented with 0.3 volume of air per volume of medium per minute of a 2% $CO_2$ in air mixture containing close to 20% $O_2$. For the helix tubular photobioreactor (helix PBR), only $CO_2$ (no air) was deliberately added to the culture, and the culture medium was amended with only glucose. The only significant source of $O_2$ for oxidative metabolism in the helix PBR under these conditions is the photosynthetic water splitting reaction at photosystem II. Flat panel PBRs were mixed by turbulent gas flow (2% $CO_2$ in air) supplied at 0.3 VVM (volume of gas per volume of culture fluid per minute). The Helix PBR was mixed by via liquid pump driven circulation without introduction of air or other source of $O_2$. Cell densities ranges are provided to demonstrate the range of values tested. Higher cell densities can be expected under higher light conditions. The range of cell densities do not represent the maximum or minimum possible values Light was provided from natural sunlight only (Flat Panel reactors) or from natural sunlight and artificial lights in the greenhouse Helix PBR installation (24 Sun Blaze T5HO-48 systems, Vancouver, WA) providing 200-1300 µmol of photosynthetically active radiation/m²/s.

The cultures were also tested in an illuminated 550-L glass tubular photobioreactor located in a greenhouse at the ASU Polytechnic Campus in Mesa, AZ. The same modified CM was used. During autotrophic growth, $CO_2$ was added at 0.2 to 0.8 L/min and excess $O_2$ was automatically purged via a dinitrogen gas input activated when a dissolved $O_2$ sensor detected 10 parts per million (PPM) $O_2$. For mixotrophic growth, glucose was amended at concentrations ranging from 6 to 24 mM, and when glucose was present, the provision of $CO_2$ was stopped. Replicates were obtained by using limiting amounts of glucose that were completely consumed in 4-10 hours followed by repetitions on the following days. These repetitions were conducted 10 times with glucose additions between 5 and 12 mM.

2. Analysis

Cell densities of the seed cultures were measured spectrometrically (750 nm). Ash-free dry weights, optical density (629, 680, and 750 nm), Fv/Fm, and the nutrient (glucose, nitrogen and phosphorus) content in the supernatant was determined for each sample. Each treatment was tested in triplicate.

To directly monitor PS-II activity we used PAM fluorescence techniques to measure $F_v/F_m$, also known as photosynethetic efficiency.

3. Results

The productivity and photosynthesis rates of a strain of Galdieria sulphuraria in two types of culture system (flat-panel photobioreactor and helix tubular photobioreactor) are compared in Table 2.

TABLE 2

Performance parameters from flat panel PBR (excess $O_2$) and a helix tubular PBR (microaerobic)

| Photobioreactor and Date Range | Starting Cell Density g/L | Ending Cell Density g/L | Average $F_v/F_m$ | Productivity g/L/Day | Substrate Yield g biomass/g glucose consumed |
|---|---|---|---|---|---|
| Flat Panel-PBR May 30-June 4 | 1.18 | 5.85 | 0.2-0.45 | 1.2 | 0.43 |
| Helix Tubular PBR November 15-17 Mean of 3 successive days | 2.36 | 3.56 | 0.74 | 1.37 | 0.97 |
| Helix Tubular PBR August 31-September 3 Values are the mean for the 4-day incubation | 2.2-5.4 | 2.9-5.8 | 0.67 | 1.58 | 0.57 |

The measured maximum photosynthetic efficiency under low $O_2$ conditions in the helix PBR is twice as high (0.67-0.74) as in the high-$O_2$ flat panel PBRs and much higher than the values reported by Oesterhelt et al. (0.41) for a different G. sulphuraria strain incubated in the presence of glucose and excess $O_2$. For comparison, $F_v/F_m$ values above 0.5 were not observed in the Flat Panel PBR experiments. The high mixotrophic photosynethetic efficiency values observed the Helix PBR cultures also persist for at least 4 days of mixotrophic cultivation. We conclude that catabolic repression of photosynthesis by mixotrophic substrates does not occur when photosynthesis is the source of oxygen for mitochondrial function during mixotrophic growth.

Substrate yields provide another metric to assess the value of the invention. Purely heterotrophic (dark) substrate yields for G. sulphuraria have been reported in the 0.42-0.45 range (Graverholt et al. and Schmidt et al.). As shown in Table 2, substrate yields in the Flat Panel conditions with excess oxygen produce similar substrate yields suggesting little benefit to mixotrophy in this particular experiment. However, the substrate yield was 2.25 times higher in the Helix PBR with limited external oxygen supply over the first 3 days of growth. Substrate yield dropped to 1.3 times higher than the Flat Panel value as the cell density rose over the following 4 days. This could be due to light attenuation at higher cell densities.

Three different isolates of G. sulphuraria (strains 5587.1, 107.79, and 29.92) responded in the same manner to aerobic and microaerobic mixotrophy (FIG. 2). As there was residual glucose present for all three strains at 24 hours, this was the time interval for determining substrate yields. As shown in Table 3, the 107.79 strain was the most productive strain of the three based on growth rate and glucose uptake rates.

TABLE 3

Substrate yields for the mixotrophic treatment of the cultures depicted in FIG. 2.

| Strains | Treatment | 24 hour Substrate Yields (g biomass/g glucose) |
| --- | --- | --- |
| G. sulphuraria 5587.1 | Photoautotrophic | |
| G. sulphuraria 5587.1 | Mixotrophic-aerobic | 0.595 |
| G. sulphuraria 5587.1 | Mixotrophic-microaerobic | 0.809 |
| G. sulphuraria 29 | Photoautotrophic | |
| G. sulphuraria 29 | Mixotrophic-aerobic | 0.849 |
| G. sulphuraria 29 | Mixotrophic-microaerobic | 1.034 |
| G. sulphuraria 107 | Photoautotrophic | |
| G. sulphuraria 107 | Mixotrophic-aerobic | 0.916 |
| G. sulphuraria 107 | Mixotrophic-microaerobic | 0.901 |

Figure 3:
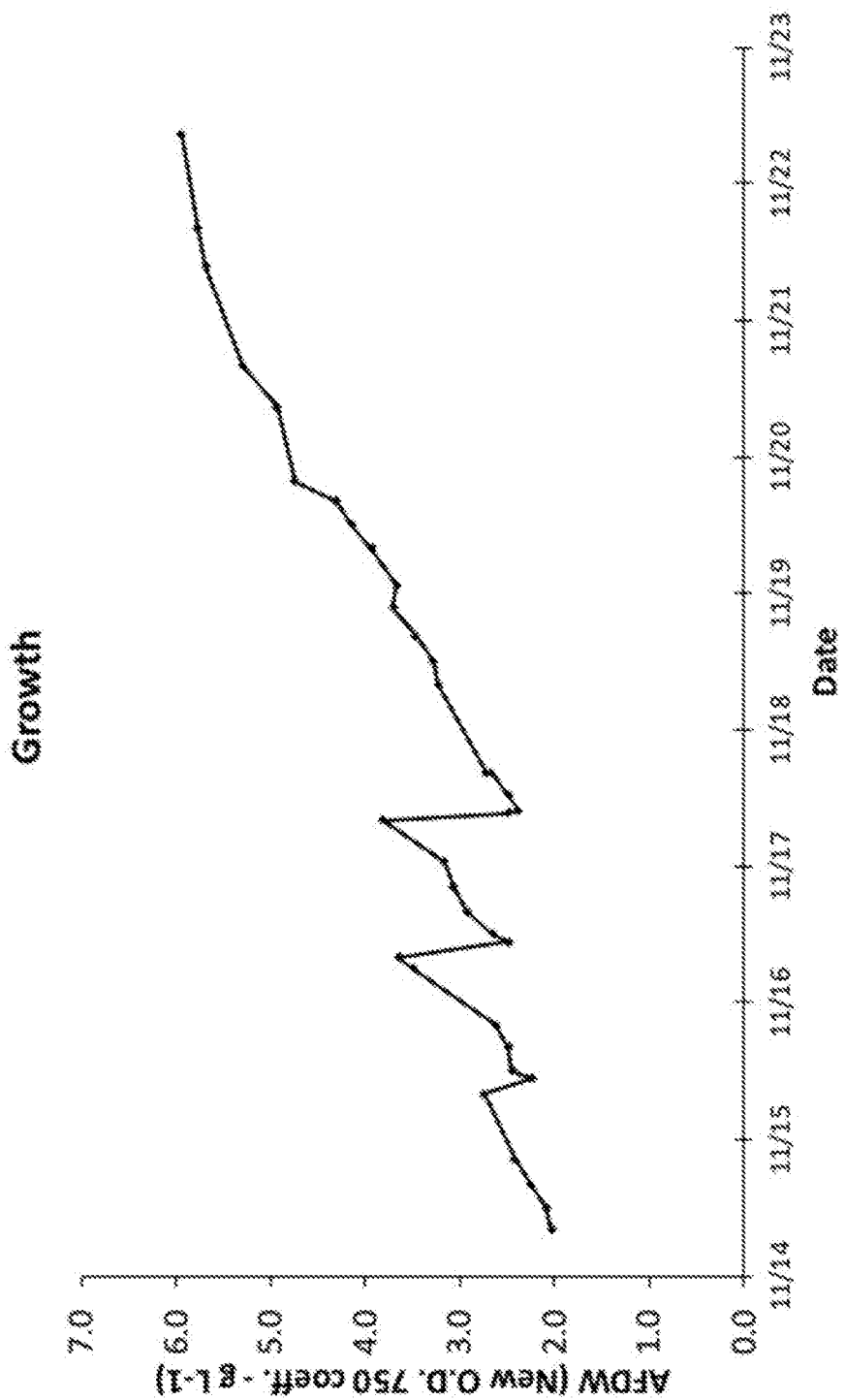
FIG. 3 depicts the effect on AFDW of a culture of *Galdieria sulphuraria* grown in 6 mM glucose followed by excess glucose (12 mM). The culture was diluted daily until 11/17.

The methods of the invention were tested on a strain of G. sulphuraria in a helix tubular photobioreactor under conditions of microaerobic mixtrophy. In fed-batch experiments, excess glucose (12 mM) was added at 9 AM each morning. FIG. 3 and Table 4 shows the results of this study. The Fv/Fm values were expected to drop to less than 0.30 over the four-day period if glucose mediated catabolic repression of photosynthesis was occurring as this value represents the photosynthetic efficiency of the culture. However, Fv/Fm values were not decreased in the helix tubular photobioreactor. In comparison, the bubble column values ranged from 0.2 to 0.45 after sugar consumption (see Table 2). Further evidence that catabolic repression is relieved under limiting $O_2$ conditions is the fact that subtract yields averaged 1.0 g biomass/g glucose in the helix tubular photobioreactor while the substrate yield in the flat panel photobioreactor was between 0.43-0.65 g biomass/g glucose. In fact, the substrate yield of G. sulphuraria in a helix tubular photobioreactor cultured under the conditions of the invention is roughly twice the reported substrate yields of aerobic, heterotrophic cultivation of this strain of G. sulphuraria (Graverhold and Eriksen and Schmidt et al.).

TABLE 4

Helix tubular PBR microaerobic mixotrophy.

| Start Date | Starting Cell Density g/L | Ending Cell Density g/L | Average $F_v/F_m$ | Productivity g/L/Day | Substrate Yield g biomass/g glucose consumed |
| --- | --- | --- | --- | --- | --- |
| November 14 | 2.03 | 2.42 | 0.57 | 0.81 | 0.7 |
| November 15 | 2.24 | 3.65 | 0.6 | 1.61 | 1.06 |
| November 16 | 2.48 | 3.81 | 0.76 | 1.52 | 1.14 |
| November 17 | 2.38 | 3.23 | 0.85 | 0.97 | 0.7 |
| November 18-21 | 3.23 | 5.69 | 0.83 | 0.82 | 0.83 |

4. Microaerobic Conditions Enable Algal Mixotrophy

Figure 4:
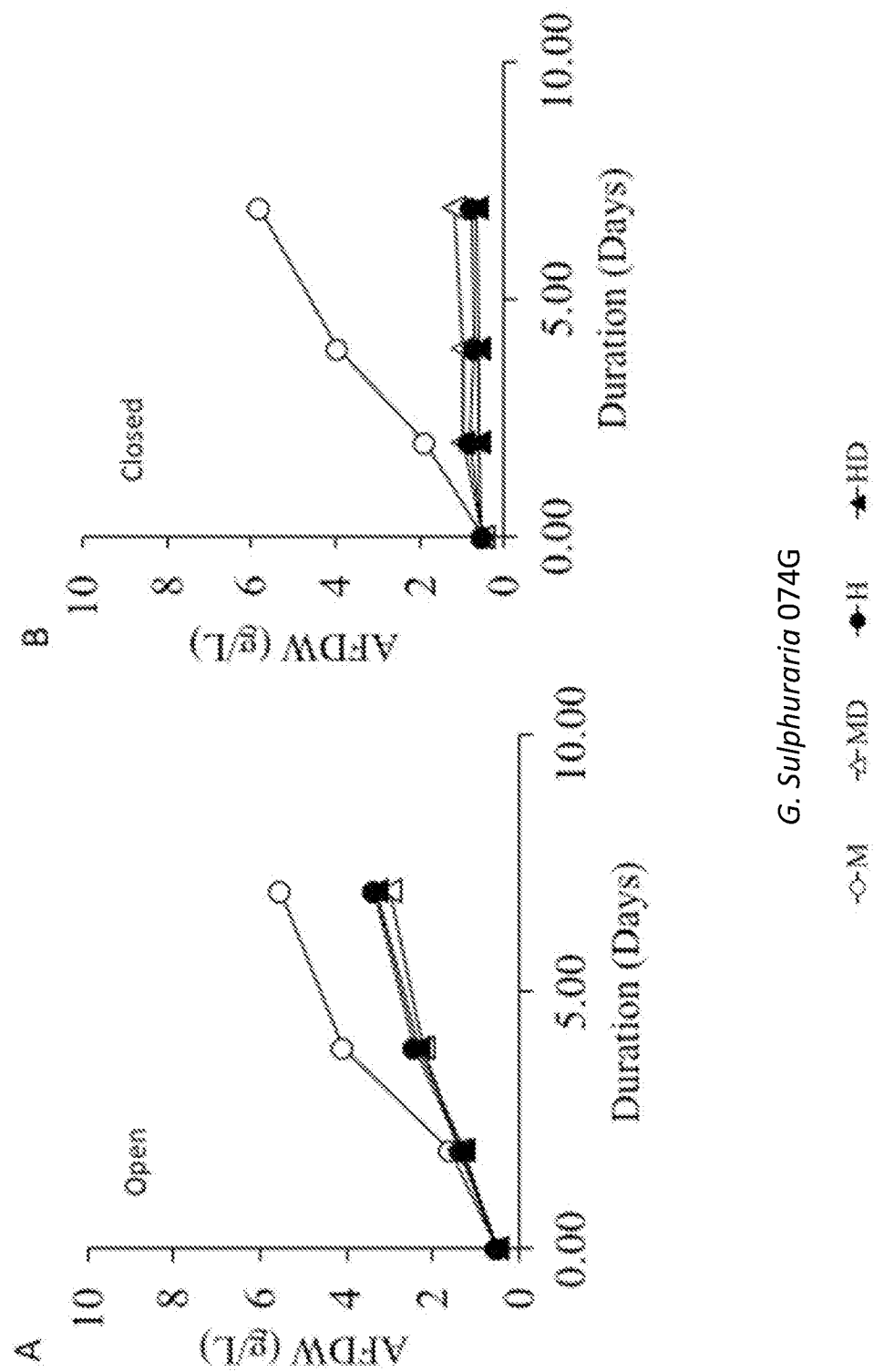
FIG. 4 and FIG. 5 depict the effect of an open culture system versus a closed culture system on the growth rate of *G. sulphuraria* 074G (FIG. 4 panels A and B) and of *G. sulphuraria* 5578.1 (FIG. 5 panels A and B) grown in mixotrophic or heterotrophic cultures. Triplicate test tube cultures (8 mL culture volume in 16 mL tubes) were inoculated with *G. sulphuraria* 074G and incubated in an open (O) or closed (C, tightly sealed) as indicated. The temperature was held at 42° C. for seven days. Mixotrophic cultures (M) were maintained in a lighted incubator while heterotrophic cultures (H) were maintained in the dark. Each treatment was carried out with a photosystem II inhibitor DCMU (3-(3,4-dichlorophenyl)-1,1-dimethylurea) treatment (D) and a control condition without the inhibitor. For example MCD represents a mixotrophic culture grown in closed test tubes in the presence of DCMU. In the closed configuration, only the MO condition allowed for growth. The cell density (yield) after seven days was similar to the MO configuration for both strains.
Figure 5:
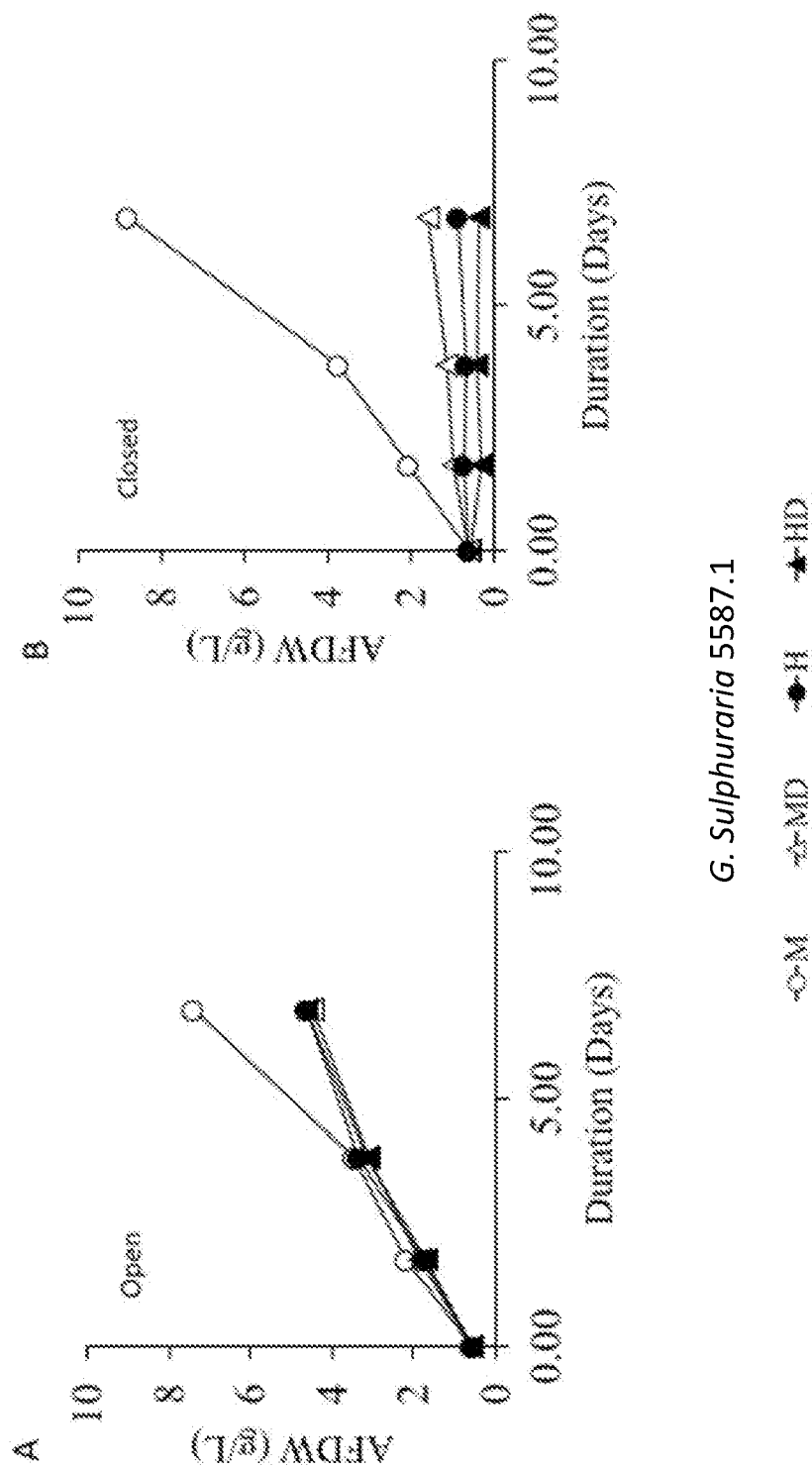

Triplicate test tube cultures (8 mL culture volume in 16 mL tubes) were inoculated with two strains of Galdieria sulphuraria and incubated in an open mode (O) or tightly sealed, closed mode (C). The incubation temperature was held at 42° C. for seven days. Mixotrophic cultures (M) were maintained in a lighted incubator while heterotrophic cultures (H) were maintained in the dark. Each treatment was carried out with a photosystem II inhibitor DCMU (3-(3,4-dichlorophenyl)-1,1-dimethylurea) treatment and a control condition without the inhibitor. As indicated in the drawing description and on FIGS. 4 and 5, the control conditions are labeled M or H for mixotrophic culture and heterotrophic culture, respectively. Thus, the treatment groups are correspondingly labeled MD or HD.

As shown in FIG. 5B, only the mixotrophic culture in control condition allowed for growth. For both strains of G. sulphuraria, the cell density (yield) after seven days of the mixotrophic culture grown control condition was similar.

REFERENCES CITED

1. Oesterhelt, C., et al. *Regulation of photosynthesis in the unicellular acidophilic red alga Galdieria sulphuraria*. Plant Journal, 2007. 51(3): p. 500-511.
2. Stadnnichuk, I., et al., *Inhibition by glucose of chlorophyll a and phycocyanobilin biosynthesis in the unicellular red alga Galdieria partita at the stage of coproporphyrinogen III formation*. Plant Science, 1998. 136(1): p. 11-23.
3. Bader, K. P. and G. H. Schmid (1989). "Photosynthetic and respiratory oxygen gas-exchange measured by mass-spectrometry in the filamentous cyanobacterium oscillatoria-chalybea in dependence on the nitrogen-source in the growth-medium." Biochimica Et Biophysica Acta 974(3): 303-310.
4. Graverholt, O. S. and N. T. Eriksen, *Heterotrophic high-cell-density fed-batch and continuous-flow cultures of Galdieria sulphuraria and production of phycocyanin*. Applied Microbiology and Biotechnology, 2007. 77(1): p. 69-75.
5. Sorensen, L., A. Hantke, and N. T. Eriksen, *Purification of the photosynthetic pigment C-phycocyanin from heterotrophic Galdieria sulphuraria*. J Sci Food Agric, 2013. 93(12): p. 2933-8.
6. Schonknecht, G., et al., *Gene Transfer from Bacteria and Archaea Facilitated Evolution of an Extremophilic Eukaryote*. Science, 2013. 339(6124): p. 1207-1210.

The invention claimed is:

1. A method of increasing algae biomass productivity in an algae culture comprising Cyanidiophyceae, the method comprising:
   introducing a feedstock comprising a mixotrophic substrate to an algae culture when the algae culture is exposed to light at an intensity sufficient to support photosynthesis;
   not providing supplemental $O_2$ to the algae culture; and
   not providing supplemental $CO_2$ to the algae culture,
   wherein the algae culture is in a closed culture system.

2. The method of claim 1, wherein the intensity of light sufficient to support photosynthesis is greater than 50 µmol photosynthetically active radiation per square meter per second.

3. The method of claim 1, wherein the stoichiometric oxygen supply of the algae culture is less than the stoichiometric carbon concentration introduced into the algae culture by the mixotrophic substrate in the feedstock as defined by the equation $CO_2 + H_2O + PAR \Leftrightarrow CH_2O + O_2$.

4. The method of claim 1, wherein the mixotrophic substrate comprises wastewater.

5. The method of claim 1, wherein the algae is mixotrophic.

6. The method of claim 1, wherein the algae is thermophilic, acidophilic, or both.

\* \* \* \* \*